United States Patent [19]
Schlitt

[11] Patent Number: 5,474,534
[45] Date of Patent: Dec. 12, 1995

[54] INDWELLING CATHETER

[76] Inventor: Michael J. Schlitt, 10521 SE. 29th St., Bellevue, Wash. 98004

[21] Appl. No.: 266,297

[22] Filed: Jun. 27, 1994

[51] Int. Cl.$^6$ .................. A61M 31/00; A61M 5/178; A61M 5/32
[52] U.S. Cl. .............. 604/49; 604/164; 604/177
[58] Field of Search .................. 604/164–170, 604/263, 174, 177, 178, 180, 49–53

[56] References Cited

U.S. PATENT DOCUMENTS

| | | | |
|---|---|---|---|
| 2,725,058 | 11/1955 | Rathkey | 604/177 |
| 3,589,361 | 6/1971 | Loper et al. | 604/177 X |
| 4,326,519 | 4/1982 | D'Alo et al. | 604/177 X |
| 4,368,738 | 1/1983 | Tersteegen et al. | 604/180 |
| 4,445,893 | 5/1984 | Bodicky | 604/165 |
| 4,563,177 | 1/1986 | Kamen | 604/177 |
| 4,863,432 | 9/1989 | Kvalo | 604/177 |
| 5,190,528 | 3/1993 | Fonger et al. | 604/171 |

Primary Examiner—John D. Yasko
Assistant Examiner—Adam J. Cermak
Attorney, Agent, or Firm—Christopher Duffy

[57] ABSTRACT

The proximal end portion 29 of the relatively outer cannula 6 of the catheter 2 has a pusher tab 44 relatively radially upstanding on the cylindrical surface 32 thereof, which projects relatively radially outwardly from the cylindrical outline of the relatively outer cannula at the outer periphery thereof, to the extent that when a user grips the hilt 54 of the relatively inner cannula 4 with one hand 70 to advance the distal end portion 36 of the relatively outer cannula into a vein 80 or other passage and disengage the relatively inner cannula from the bore of the relatively outer cannula, he/she can apply one finger of his/her one hand, such as the index finger 72 thereof, to the tab, to drive the relatively outer cannula relatively forward toward the puncture 98 in the skin 78. The tab is limited in angular extent about the axis of the relatively outer cannula, however, so that after it has been angularly oriented about the axis 38 of the relatively outer cannula to upstand at a location opposite the skin for the advancement and insertion step, the relatively outer cannula can be rotated about its axis to lay the tab over against the skin while a strip of adhesive tape 96 or the like is applied over the tab to secure the relatively outer cannula to the skin, both lengthwise and crosswise of the axis, as well as rotationally thereof.

16 Claims, 4 Drawing Sheets

INDWELLING CATHETER

TECHNICAL FIELD

This invention relates to a catheter which is insertable into a subcutaneous passage in the body of a human or animal recipient which is living or has been recently living, for indwelling therein while blood or other liquid is transmitted through the catheter between the passage and an auxiliary apparatus external to the recipient. In particular, it relates to an intravenous catheter, that is, one which is insertable into a subcutaneous vein, artery or other blood vessel of a recipient, for the infusion of a liquid into his, her or its blood stream from an intravenous liquid supply external to the recipient, or for the withdrawal of blood from the blood stream, or perhaps for simply monitoring some condition of the stream, such as the pressure thereof.

BACKGROUND ART

Intravenous catheters have been available for many years, but have undergone virtually little or no change all those years, despite certain shortcomings which, though commonly tolerated, have rendered them less than full serviceable for their intended purpose. In general, each comprises a pair of elongated relatively inner and outer cannulae which have longitudinal axes and elongated bores extending therethrough along the axes thereof, and the relatively inner of which cannulae is telescopically engageable in and disengageable from the bore of the relatively outer cannula when the respective cannulae are coaxially aligned with one another along the respective longitudinal axes thereof. The relatively outer cannula has relatively proximal and distal ends spaced apart from one another along the longitudinal axis thereof, an outer periphery circumposed about the longitudinal axis thereof between the respective ends thereof, a cylindrical outline at the outer periphery thereof, and a cylindrical surface circumposed about the longitudinal axis thereof on the cylindrical outline thereof. The relatively inner cannula has a needle-like shank which is telescopically engageable in and through the bore of the relatively outer cannula from the proximal end thereof, and a hilt which is disposed on the shank and adapted to abut the proximal end of the relatively outer cannula when the shank has extended through the bore of the relatively outer cannula to the extent that the shank projects relatively outwardly beyond the distal end of the relatively outer cannula to form a puncturing tip thereon for the catheter. In use, the relatively inner cannula is telescopically engaged in the relatively outer cannula, to form a unitary assembly of the two cannulae, and then while the assembly is held in one hand, the puncturing tip of the relatively inner cannula and the distal end of the relatively outer cannula are bayonetted through the skin of a recipient until the tip and end of the respective cannulae are inserted in a blood vessel below the skin, but carefully kept in line with the path of the blood vessel and maintained at a relatively shallow angle of incidence to the skin so as not to puncture any of the lateral or ventral sides of the blood vessel. Then, while the hilt of the relatively inner cannula is held by the more ulnar fingers and thumb of that one hand, the index finger of the one hand is engaged with the proximal end portion of the relatively outer cannula, and the relatively outer cannula is driven into the puncture in the skin with the index finger, and relatively lengthwise into the blood vessel itself, to advance the distal end portion of the relatively outer cannula into the blood vessel and disengage the relatively outer cannula from the relatively inner cannula and vice versa. This done, the relatively outer cannula is then interconnected with an auxiliary apparatus external to the body of the recipient, for the transmission of a liquid to the vessel, or the transmission of blood from the vessel, or the monitoring of the condition of the blood in some way; and the connection is commonly made by inserting a fitting on a piece of flexible tubing running from the apparatus, into the proximal end portion of the relatively outer cannula, or vice versa, to form a male/female joint between the tubing and the relatively outer cannula. The entire procedure is, of course, a delicate one in that the catheter and the respective components thereof, are diminutive in size, and are difficult to grasp and manipulate during the various steps of the procedure. Also, if the procedure is to be entirely efficacious, the tip of the relatively inner cannula and the distal end of the relatively outer cannula must be inserted in the blood vessel, and the relatively outer cannula advanced within the blood vessel, lengthwise thereof, without the tip or end of either cannula puncturing the lateral or ventral sides of the blood vessel during the installation procedure. And if the installation is to be comfortable to the recipient, not only must the relatively outer cannula be properly installed in the blood vessel lengthwise thereof, without puncturing any of the lateral or ventral sides of the vessel, but in addition, the relatively outer cannula must be secured against being jiggled in the vessel, side to side or up and down thereof, such as when the recipient moves with a lurch, or worse yet, moves in such relationship to the auxiliary apparatus as to cause the connection to swing the proximal end portion of the relatively outer cannula sidewise of the puncture in the dorsal side of the blood vessel. Commonly, the risk of such relative movement between the body of the recipient, on one hand, and the relatively outer cannula, on the other, has been abated in part by securing a strip of adhesive tape over the joint between the tubing and the relatively outer cannula, that is, at the point at which the moment arm of the relatively outer cannula is greatest. But while this strategy has been somewhat effective to prevent relative movement between the two, it has also posed a problem for those who are responsible for the care of the recipient during the indwelling of the catheter. The tubing requires replacing from time to time, and each person responsible for replacing the tubing must first remove the strip of adhesive tape to access the joint for the replacement operation. In addition, a sterile gauze, such as a BANDAID brand of skin attachable protective gauze, is commonly placed over the puncture in the skin of the recipient, to protect it against infection, and while this may be spaced apart from the joint and not interfere with the task of replacing the tubing, it is important that any different technique for securing the catheter in place, not interfere with a decision to replace the gauze also, when replacing the tubing.

Given their diminutive size, catheters are best installed by persons who have nimble fingers and thumbs and the dexterity to effect the installation procedure. The ability to use the fingernail of the index finger as a driver or pusher is also an asset, in that it is common practice to effect the advancement of the relatively outer cannula into the blood vessel, by engaging the proximal end portion of the relatively outer cannula with the fingernail of the index finger, and then "uncoiling" the finger to drive the relatively outer cannula up into the blood vessel lengthwise thereof. Women in particular have more nimble fingers, and are more dexterous with their finger tips. They often can also make a better purchase of things they grasp, particularly small things such as catheters. But many anesthesiologists and surgical assistants, and particularly those of the male gender, have more fleshy fingers and thumbs, and are less agile with their fingers and fingernails. For them, the delicate operation of grasping the catheter, bayonetting it into a blood vessel of a recipient, and then advancing the relatively outer cannula up the length of the blood vessel, is not one they can accomplish with ease. Moreover, their task is further complicated by the fact that the blood vessel commonly chosen for the installation, is a vein adjacent the upper side of one hand of the recipient, and the anesthesiologist or other professional effecting the installation, commonly must grasp that one hand of the recipient with his or her other hand, to steady it and spread the skin, while grasping and manipulating the catheter with his or her one hand during the installation process; and any clumsiness on the part of the professional is an additional irritant to the recipient, particularly when the professional effects the step of advancing the relatively outer cannula up the length of the vein of the recipient, i.e., the most delicate step in the procedure.

DISCLOSURE OF THE INVENTION

According to my invention, to rid catheters of these shortcomings, I give the proximal end portion of the relatively outer cannula a pusher tab which relatively radially upstands on the cylindrical surface thereof, and projects relatively radially outwardly from the cylindrical outline of the relatively outer cannula at the outer periphery thereof, to the extent that when a user grips the hilt of the relatively inner cannula with one hand to advance the distal end portion of the relatively outer cannula up the length of a blood vessel and disengage the relatively inner cannula from the bore of the relatively outer cannula, he or she can apply one finger of his or her one hand, such as the index finger thereof, to the tab, to use the greater stature and authority of the tab in driving the relatively outer cannula relatively forward toward the puncture in the skin. This enables him or her not only to drive the relatively outer cannula off the relatively inner cannula with greater thrust and certainty of purpose, but also to do so with greater accuracy of purpose, so that as he or she drives the relatively outer cannula up the length of the blood vessel in the recipient, he can take greater care not to veer off from the path of the blood vessel. The pusher tab also has one or more additional functions, I might add, in that I make the tab less than a quadrant in angular extent about the proximal end portion of the relatively outer cannula circumferentially thereof, so that during the advancement of the distal end portion of the relatively outer cannula into the blood vessel of the recipient, the tab can be angularly oriented about the axis of the relatively outer cannula to upstand at a location on the opposite side of the axis of the relatively outer cannula from the skin of the recipient, where the tab will not scrape or otherwise irritate the skin of the recipient, but afterward, when the distal end portion of the relatively outer cannula is fully inserted in the blood vessel below the skin, the relatively outer cannula can be rotated about the axis thereof to lay the tab over against the skin of the recipient while skin attachable hold-down means such as a piece of adhesive faced sheet material, are applied over the tab to detachably secure the relatively outer cannula to the skin, at least crosswise of its axis and rotationally thereof, if not also longitudinally of its axis. In this way then, the tab forms not only a driver with which to advance the relatively outer cannula and disengage the respective cannulae from one another, but also an outrigger with which to directly but detachably secure the relatively outer cannula to the skin of the recipient, and in all directions if desired, that is, longitudinally, transversely, and rotationally of the cannula. However, in addition to those functions, the tab may also function as an indicator of the degree of advancement of the relatively outer cannula into the blood vessel of the recipient; and/or as a means for rotating the relatively outer cannula relative to the tubing, and vice versa, when the fitting on the tubing is engaged with the proximal end portion of the relatively outer cannula in making a male/female connection between the tubing and the cannula to prepare the cannula for the liquid or blood transmission process. In fact, the tab may also be used to enable the user to gain a greater purchase on the unitary assembly of the two cannulae during the bayonetting and insertion step, if desired, since the thumb and one finger of the hand with which the unitary assembly is bayonetted into the skin of the recipient, may be clamped about the tab, if desired, while the remaining fingers of that hand are wrapped about the hilt of the relatively inner cannula, rearwardly thereof, to obtain a more wide spread grip on the assembly, if desired. This also has the effect of preserving the orientation of the tab, relative to the skin of the recipient, during the bayonetting and insertion step. And finally, in the packaging of the catheter, the tab may function as a means with which to snap-engage the catheter in a scabbard or the like, for the protection of the catheter during the shipment, sale and storage thereof, prior to use.

In many of the presently preferred embodiments of my invention, the tab takes the form of a stud which is spaced apart from the proximal end of the relatively outer cannula, forwardly of its axis on the cylindrical surface thereof, and is ancipital longitudinally of the relatively outer cannula, that is, substantially flat and double-edged longitudinally of the relatively outer cannula. In certain embodiments, moreover, so as to lend itself better to the securement step, the stud has a relatively reduced diameter neck which is relatively radially upstanding on the surface of the proximal end portion of the relatively outer cannula, in an axial plane thereof, and has a head at the top thereof, which is supported on the neck and is relatively enlarged to it in the axial plane of the relatively outer cannula.

Commonly, and as in the past, the proximal and distal end portions of the relatively outer cannula are relatively enlarged and reduced in diameter, respectively, at the cylindrical surface of the relatively outer cannula, so that the distal end portion of the relatively outer cannula forms a puncture insertable sheath for the shank of the relatively inner cannula, and the proximal end portion of the relatively outer cannula forms a relatively radially enlarged hub at the proximal end of the sheath, for a tubular extension on an annular boss at the forward end of the hilt of the relatively inner cannula, which is telescopically engageable with the hub when the relatively inner cannula is telescopically engaged in the relatively outer cannula.

The proximal end portion or hub of the relatively outer cannula may also have other relatively raised relief thereon, that is, other than the tab. For example, the cylindrical surface on the proximal end portion of the relatively outer cannula may have an annular flange circumposed thereabout at the proximal end of the relatively outer cannula, to form a relatively radially enlarged abutment surface for the forward end of the hilt of the relatively inner cannula; but if so, the flange projects relatively radially outwardly from the cylindrical surface on the proximal end portion of the relatively outer cannula, to a substantially lesser extent than the tab.

BRIEF DESCRIPTION OF THE DRAWINGS

These features will be better understood by reference to the accompanying drawings wherein I have illustrated one of the presently preferred embodiments of my invention and its installation and use in a subcutaneous vein of a recipient's hand.

In the drawings.

BEST MODE FOR CARRYING OUT THE INVENTION

Figures 1, 2:
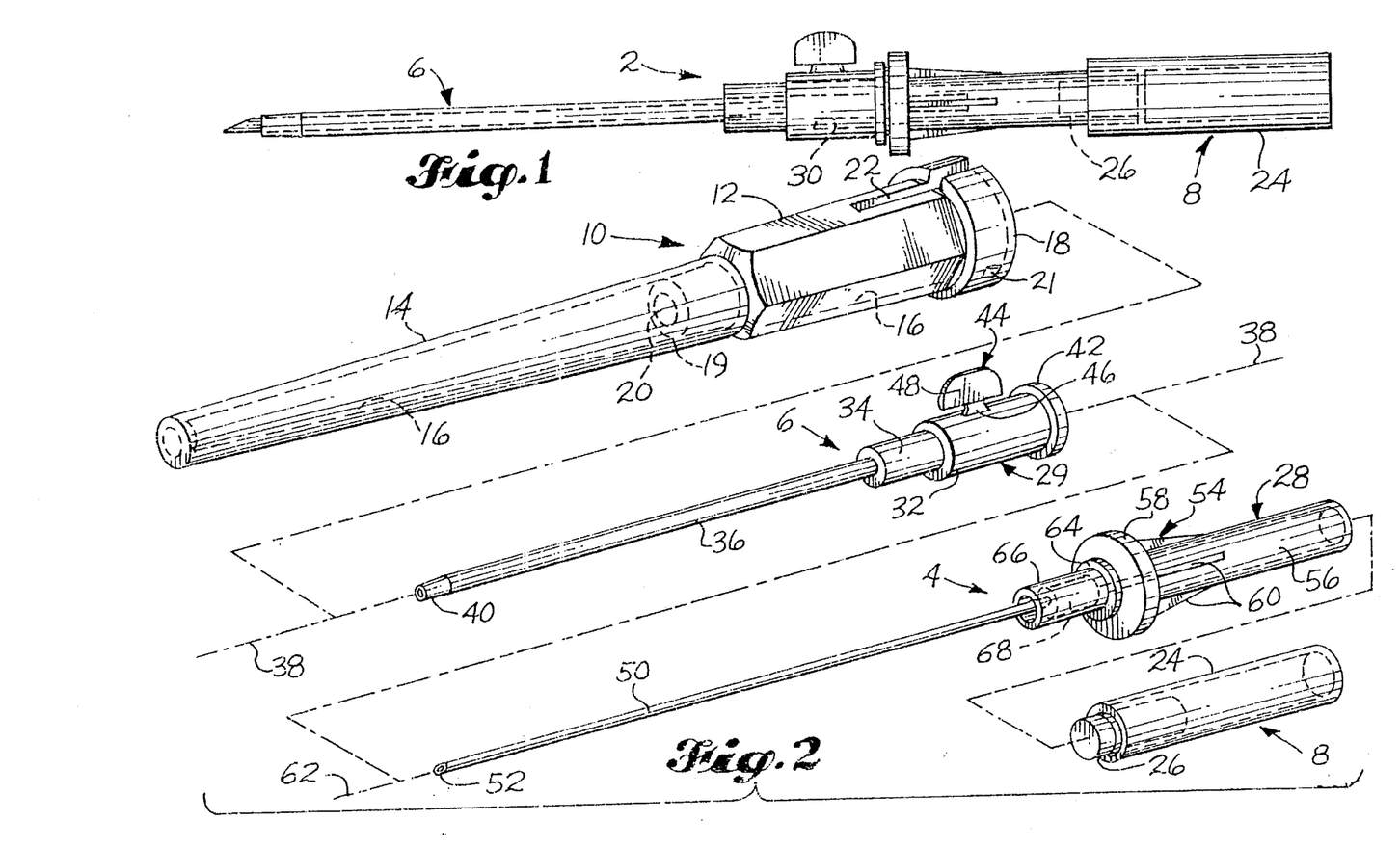
FIG. 1 is a side elevational view of the embodiment when the respective cannulae thereof are telescopically engaged with one another as a unitary assembly for the bayonetting step of the installation process, and a plug has been inserted in the hilt of the relatively inner cannula to limit the escape of blood from the vein when the assembly has been inserted therein during the process.
FIG. 2 is an exploded perspective view not only of the respective cannulae in the catheter, and the plug for the relatively inner cannula, but also of a plastic scabbard for holding the catheter during the transportation, sale, and storage of the same prior to the use thereof.
Figures 3, 5, 8:
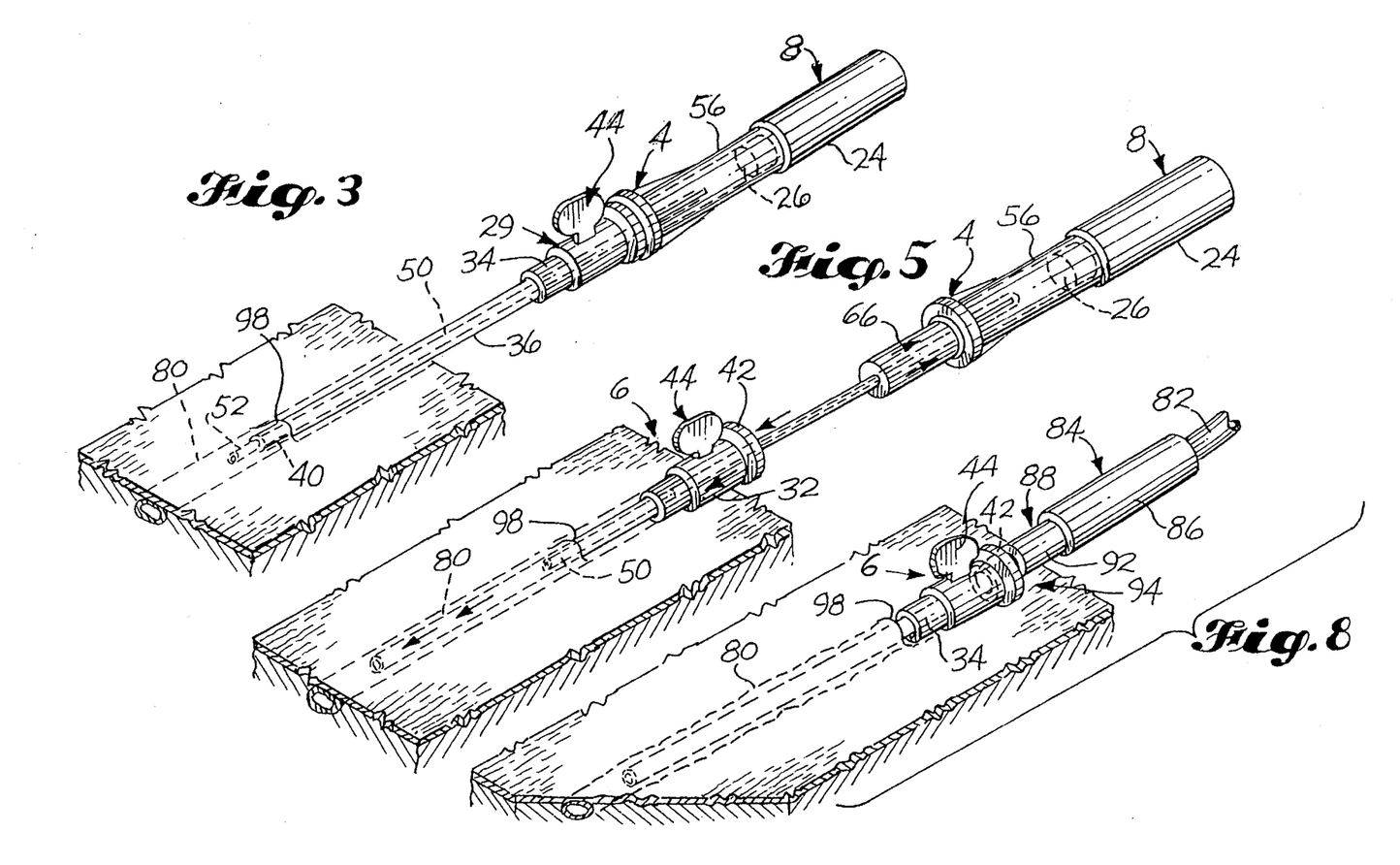
FIG. 3 is a perspective view of the catheter at a time when the puncturing tip of the relatively inner cannula and the distal end of the relatively outer cannula, have been bayonetted through the skin of the recipient's hand, and inserted in the targeted vein thereunder, at a low angle of incidence to the skin of the recipient's hand.
FIG. 5 is a perspective view of the catheter alone at this latter point in time, but on the scale of FIG. 3, to more closely illustrate the completion of the insertion step.
FIG. 8 is a perspective view of the relatively outer cannula on the scale of FIGS. 3 and 5 but now showing the male/female joint made between the male fitting of the flexible tubing and the proximal end portion of the relatively outer cannula, when the two have been interengaged with one another in the manner of FIG. 7, but the pusher tab has yet to be laid over against the recipient's skin for the securement step.

Referring first to FIGS. 1 and 2, it will be seen that the relatively inner and outer cannulae of the catheter 2 are identified generally by numerals 4 and 6, respectively. The plug is identified by numeral 8, and the plastic scabbard for the assembled cannulae by numeral 10. The scabbard 10 comprises a hexagonal case 12 with an elongated stem 14 at the forward end thereof. At the inside, the case and stem have an elongated socket 16 therein, which is tapered toward the tip of the stem and counterbored to a larger diameter within the case. The case also has a wide banded rim 18 around the proximal end thereof; and seated in the throat of the socket at the bottom of the counterbore is a sleeve 19 with a small diameter bore 20 therethrough. The bore 20 is adapted to slidably receive the forward end portion of the relatively outer cannula 6 of the catheter, when the respective cannulae are telescopically engaged with one another and bayonetted into the scabbard 10 at the proximal end thereof. The rim of the scabbard 18, meanwhile, has nubs 21 formed at symmetrically arrayed sites about the inner periphery thereof, which snap engage with a portion of the relatively inner cannula 4 of the assembly when the assembly is fully inserted within the scabbard, as shall be explained. In addition, the case of the scabbard has a slot 22 therein, which opens to the proximal end of the scabbard and coincides with one axial plane thereof, to accommodate a pusher tab feature of my invention that shall also be explained shortly.

The plug 8 comprises a cylindrical tube 24 which has a cylindrical insert 26 engaged in the forward end thereof. The distal end portion of the insert projects beyond the end of the tube to form a stopper for the proximal end portion 28 of the relatively inner cannula 4 when the plug is engaged therewith, as shall also be explained shortly.

The relatively outer cannula 6 has a tubular hub 29 at the proximal end thereof, which has cylindrical surfaces 30 and 32, respectively, on the inner and outer peripheries thereof, and a reduced diameter neck 34 at the forward end thereof, that is also cylindrically surfaced at the inside and outside thereof. The neck 34 in turn has an elongated tubular sheath 36 at the distal end thereof, which extends along the longitudinal axis 38 of the cannula, and has a tapered tip 40 at the distal end of it. The hub 29 also has an annular flange 42 raised about the outer peripheral surface 32 thereof, and at the proximal end of the hub. And more importantly, the hub has a combination driver/outrigger stud 44 on the surface 32 thereof, which is raised considerably higher above the surface 32 than the flange 42, and at a location spaced apart forwardly of the hub from the flange. The stud is relatively radially upstanding on the surface 32 of the hub, and is ancipital longitudinally of the relatively outer cannula, that is, substantially flat and double-edged longitudinally of the cannula. Moreover, the stud has a relatively reduced diameter neck 46 at the bottom thereof, which is relatively radially upstanding on the surface 32 of the hub in the axial plane of the stud, and has a head 48 at the top thereof which is supported on the neck and relatively enlarged to it in the axial plane of the stud. The stud 44 forms a pusher tab for the relatively outer cannula, and in addition, functions as an outrigger for the cannula, in the securement of it to the recipient's hand, as shall be explained more fully hereinafter with respect to FIGS. 3–7. Both functions are possible because in the "band" of ambient atmosphere circumposed about the outer periphery of the relatively outer cannula at the surface 32 thereof, the tab 44 is less than one quadrant in angular extent about the cannula circumferentially thereof, whereas the remaining three quadrants of ambient atmosphere about the cannula are open and unobstructed circumferentially of the surface 32, and to the extent that after the tab has functioned as a pusher for the cannula, it can be rotated in unobstructed fashion about the axis of the cannula, to perform the outrigger function as well, if desired.

The relatively inner cannula 4 has an elongated tubular needle-like shank 50 with a mitered tip 52 at the distal end thereof, and a hilt 54 at the proximal end thereof, for gripping the relatively inner cannula. The hilt is dramatically oversized, relative both to the shank 50, and to the hub 29 and flange 42 of the relatively outer cannula 6, and is adapted for gripping with one hand while the catheter as a whole is bayonetted into the skin and vein of a recipient, and then the relatively outer cannula is advanced into the vein of the recipient, lengthwise thereof, as the two cannulae are disengaged from one another. Central to the hilt, and raised about the elongated tubular body 56 thereof, is a cylindrical amulet 58 which is buttressed in turn by a series of axially extending ribs 60 that are symmetrically arrayed about the longitudinal axis 62 of the cannula. The amulet 58 has an annular boss 64 on the forward end thereof, and a cylindrical extension 66 of the boss beyond that, which is also tubular to receive the proximal end portion of the shank 50. The shank is equipped in turn with a cylindrical ferule 68 at an intermediate point on the proximal end portion thereof, and is secured to the hilt by wedgingly engaging the ferule in the extension 66 of the hilt to the extent that the proximal end portion of the shank is inserted well within the hollow of the hilt at the body 56 thereof.

The stopper 26 of the plug 8 is adapted in turn to be slideably received within the body 56 of the hilt at a point behind the proximal end portion of the shank, when the plug is coaxially aligned with the two cannulae and the stopper is inserted in the body of the hilt until the tube 24 abuts against the proximal end thereof.

In assembling the catheter, the cannulae 4 and 6 are coaxially aligned with one another, and first, the shank 50 of the relatively inner cannula 4 is telescopically engaged in and through the bore in the sheath 36 of the relatively outer cannula 6, and then the extension 66 of the boss 64 on the hilt of the relatively inner cannula is telescopically engaged in the hub of the relatively outer cannula until the boss 64 itself abuts the flange 42 on the outer cannula. When the boss abuts the flange, the shank 50 has been projected slightly beyond the distal end 40 of the sheath, to form a puncturing tip for the catheter, as seen in FIG. 1.

In packaging the catheter, the two cannulae are assembled and bayonetted into the scabbard after the stud 44 has been axially aligned with the slot 22 in the rim 18 thereof. The stud is slideably received in the slot as the sheath 36 of the relatively outer cannula telescopically engages in the bore 20 in the stem 14 of the scabbard, the hub 29 of the relatively outer cannula follows the sheath into the case 12 of the scabbard, and the amulet 58 of the relatively inner cannula snap engages with the nubs 21 around the inner periphery of the case, to detachably retain the assembly in the scabbard. The plug 8 is added to the assembly at the same time, and the entire assembly of scabbard, cannulae, and plug is sold as an integral unit.

When the catheter is put to use, the user removes the assembly from the scabbard 10, and grasps the hilt 54 with one hand 70, while if desired, pinching the stud 44 of the relatively outer cannula between the index finger 72 and the thumb 74 of that one hand 70, to position the stud upright on the assembly and gain a better grasp of the assembly. Then, while the user holds the recipient's hand 76 with his or her free hand (not shown), to steady the recipient's hand and spread the skin 78 on the dorsal side of it, the user bayonets the assembly into the skin 78 at a relatively shallow angle of inclination to the skin, and above a vein 80 prominent below it. As the tip 52 of the relatively inner cannula 4, and the distal end 40 of the relatively outer cannula 6, penetrate the dorsal side of the vein, the user inclines the tip 52 and end 40 at a still shallower angle to the skin, to align them with the vein longitudinally thereof, before they can penetrate the ventral side of the vein. See FIG. 3. Next, the user places his or her index finger 72 directly behind the stud 44, axially of the cannula, to prepare for the insertion of the relatively outer cannula into the vein; and while retaining his or her grip on the hilt with the thumb and the remaining fingers 81 of that hand, the user drives the relatively outer cannula further into the vein with his or her index finger, and longitudinally thereof, while at the same time disengaging the relatively outer cannula from the relatively inner cannula, and vice versa. See FIGS. 4–6. Commonly, the index finger is reentrantly bent or coiled inwardly on itself, the fingernail and tip of the finger are placed directly behind the stud, and then the finger is "uncoiled" to drive the relatively outer cannula ahead with, so to speak, a "flick" of the finger, as in FIGS. 4 and 6.

If blood enters the body 56 of the hilt of the relatively inner cannula during this time, the plug 8 prevents the blood from discharging from the assembly.

Once the relatively outer cannula 6 is fully installed within the vein, it is ready to have an auxiliary apparatus (not shown) connected with it, either for the transmission of a liquid supply to the vein, the withdrawal of blood from the vein, the monitoring of some condition of the blood stream, or for some other purpose relating to the recipient's blood supply. The connection is made through a length of flexible tubing 82 having a male adaptor 84 at the forward end thereof for insertion in the hub 29 of the relatively outer cannula. See FIGS. 7 and 8. The adaptor 84 is similar to the plug 8, but open ended rather than closed. Like the plug, moreover, the adaptor has a hollow cylindrical tube 86 as the main body thereof, but the tube has a hollow cylindrical extension 88 on the forward end thereof, and the extension is twice reduced in diameter to form a male insert 90 for the adaptor at the forward end thereof, and an intermediate land 92 between the insert and the body of the adaptor. The land is adapted to receive a protective cap (not shown) for the forward end portion 88 of the adaptor when the tubing is packaged for marketing to the health care industry.

The male insert 90 of the adaptor is slidably insertable in the hub 29 of the relatively outer cannula, but adapted to make an interference fit with the hub, so that the connection between the outer cannula and the tubing can be made liquid tight at the joint 94 between the hub and the adaptor. After the relatively outer cannula is installed in the vein, and the relatively inner cannula is fully removed from the same, the insert 90 of the adaptor is installed in the hub of the relatively outer cannula, and if needed, the stud is employed in rotating the hub relative to the adaptor, and vice versa, for ease in achieving a liquid tight fit between the two. Then, if it was not done in achieving the fit, the relatively outer cannula is rotated about its axis 38 through approximately ninety degrees, to lay the stud over against the skin on the dorsal side of the recipient's hand; and while the stud remains in this position, a strip of adhesive tape 96 is applied over the stud, and along a parallel to the axis of the relatively outer cannula, so as to detachably secure the cannula to the recipient's hand, both longitudinally and transversely of the axis, as well as rotationally thereof. See FIG. 9. This leaves the joint 94 between the relatively outer cannula and the adaptor, uncovered, as well as the puncture 98 in the skin of the recipient's hand. A sterile but inexpensive BANDAID brand of skin attachable protective gauze 100 is commonly applied over the puncture, to protect it against infection, but since the combination of the adhesive strip and the Bandaid operate to fully secure the arrangement against both relative movement and infection, nothing further is needed for the patient's comfort and protection, including at the joint 94.

Figures 7, 10, 11:
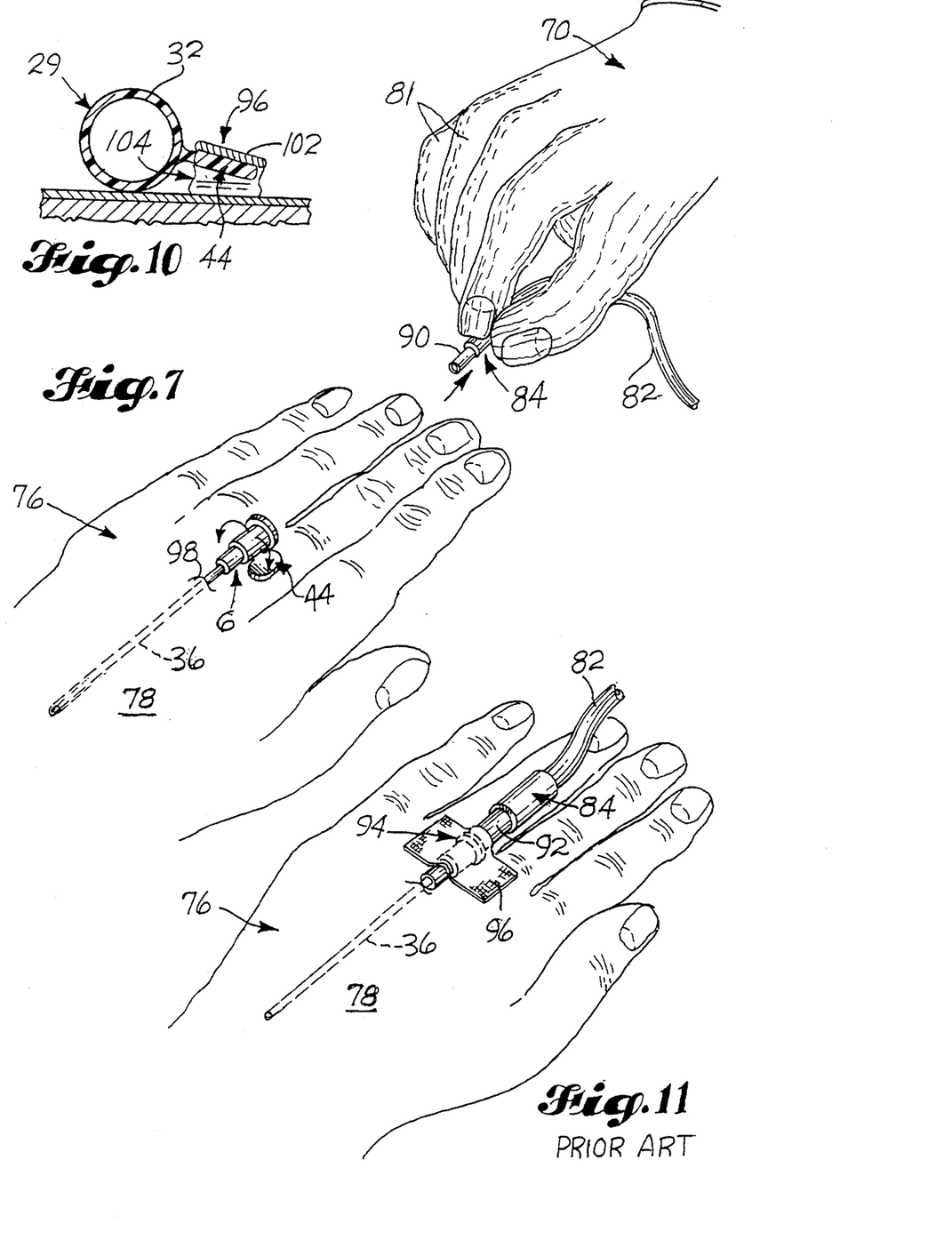
FIG. 7 is a perspective view like FIG. 4 but showing now the manner in which, using the tab, the relatively outer cannula may be rotated about its longitudinal axis to assist in interengaging it with a male fitting on a piece of flexible tubing running from a auxiliary apparatus for the catheter, and in any event, the manner in which, ultimately, the pusher tab is laid over against the skin of the recipient's hand for purposes of securing the relatively outer cannula to the recipient's hand.
FIG. 10 is a cross sectional view along the line 10—10 of FIG. 9 showing the manner in which the tab has been taped to the recipient's skin in FIG. 9 to allow for some play between the tab and the skin.
FIG. 11 is a perspective view of the hand of a recipient who has undergone a typical prior art installation in which the relatively outer cannula was secured to the skin of the recipient's hand, using a strip of adhesive tape at the joint between the male fitting on the tubing and the proximal end portion of the relatively outer cannula.

Contrast this with FIG. 11, which illustrates the practice that was commonly followed in the past to detachably secure the catheter and tubing arrangement for the recipient's comfort and protection. As seen, a strip of adhesive tape 96 was commonly applied over the joint 94 itself, to detachably secure the arrangement against relative movement, and then the puncture 98 was protected either with a BANDAID brand of skin attachable protective gauze, or with a still larger piece of sterile gauze (not shown) which was laid over the entire hub end of the cannula 6, as well as the puncture 98 and the joint 94. Of course, the adhesive strip 96 did not prevent the cannula 6 from shifting relative to the recipient's hand, longitudinally of the cannula, or rotating about the axis 38 thereof. It only prevented the hub of the cannula from shifting laterally of the puncture. Moreover, and more troublesome to health care workers, was the fact that the adhesive strip 96 overlaid that part of the arrangement which had to be accessed each time that the tubing 82 was changed thereafter during the indwelling of the catheter. Typically, the tubing 82 requires changing every twenty-four hours, and when this was done in the past, it was necessary to remove the strip 96 to access the joint 94 for purposes of disconnecting the adaptor 84 from the hub 29 of the relatively outer cannula, and then exchanging a new length of tubing 82 for the old. With the arrangement of my invention, this is no longer necessary. Now, the adaptor 84 on the used length of tubing can be removed from the hub of the outer cannula, and the adaptor of a new length of tubing can be inserted in its place to renew the arrangement, all while the outer cannula 6 remains restrained against relative movement both lengthwise and transversely of its axis, as well as rotationally thereof.

Figures 4, 6, 9:
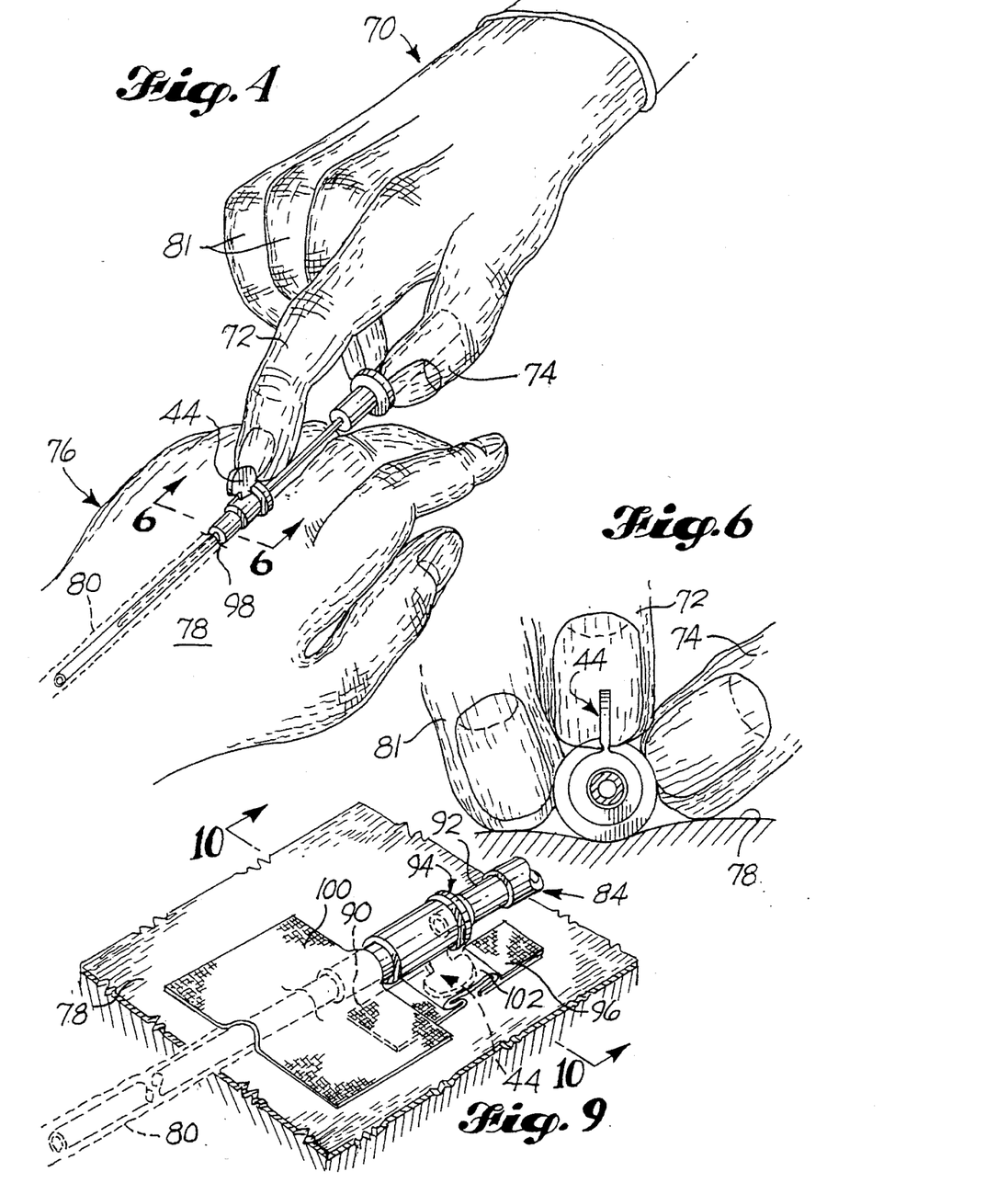
FIG. 4 is a perspective view of both the user's hand and the recipient's hand at this point in time, but showing the subsequent step of driving the relatively outer cannula up the length of the vein in the recipient's hand, with the index finger of the user's hand, while at the same time disengaging the relatively inner cannula from the relatively outer cannula and vice versa, to complete the insertion step of the installation process.
FIG. 6 is a cross sectional view along the line 6—6 of FIG. 4, showing the manner in which the index finger of the user's hand was applied to the pusher tab on the proximal end portion of the relatively outer cannula during the step of driving the relatively outer cannula up the length of the recipient's vein as the respective cannulae were disengaged from one another.
FIG. 9 is a perspective view of that portion of the recipient's hand at the puncture in the recipient's skin, but somewhat enlarged over those of FIGS. 3–8, to show one way in which the relatively outer cannula may be secured to the recipient's skin, using the tab and a strip of adhesive tape for the purpose, and in addition, a way in which the puncture itself may be secured against infection with a BANDAID brand of skin attachable protective gauze.

Preferably, at the time an adhesive strip 96 is applied to the stud 44 of my device, a "column" is fashioned in the strip to allow for a certain amount of "play" between the stud and the recipient's hand. Referring to FIGS. 9 and 10, it will be seen that the strip is raised and buckled at its center, so that the center section 102 of the strip is drawn up longitudinally thereof to form a neck 104 under the strip, which is positioned in turn under the stud, and is adapted so that a degree of "play" is possible between the stud and the skin of the recipient. This increases the level of comfort to the recipient, by avoiding pressure on his skin, and yet still enables the strip to restrain the cannula 6 against relative movement longitudinally and transversely of the axis 38 of the cannula, as well as rotationally thereof.

Where desired, my device also lends itself to using a single sterile adhesive overlay as the means for detachably securing the entire placement to the skin of the recipient's hand, including a transparent overlay such as the TEGADERM brand of transparent dressing made by the Medical-Surgical Division of 3-M Corporation, St. Paul, Minn. In such a case, the adhesive side of the overlay is applied over the stud 44 to secure it in the same manner as the tape 96, as well as over the puncture and the remainder of the relatively outer cannula to envelope the placement. The joint 94 may be left uncovered, or covered by an edge of the dressing which can be folded back when the tubing is changed.

I claim:

1. A method of installing a catheter in a subcutaneous passage in the body of a human or animal recipient which is living or has been recently living, for indwelling therein while blood or other liquid is transmitted through the catheter between the passage and an auxiliary apparatus external to the recipient, comprising:

installing in the passage, the distal end portion of an elongated cannula having a longitudinal axis and an elongated bore extending therethrough along the axis thereof, relatively proximal and distal ends spaced apart from one another along the longitudinal axis thereof, an outer periphery circumposed about the longitudinal axis thereof between the respective ends thereof, a cylindrical outline at the outer periphery thereof, and a cylindrical surface circumposed about the longitudinal axis thereof on the cylindrical outline thereof, and having moreover, an outrigger relatively radially upstanding on the cylindrical surface of the proximal end portion thereof, which is less than a quadrant in angular extent about the proximal end portion of the cannula circumferentially thereof, to upstand at a location on the opposite side of the axis of the cannula from the skin of the recipient during the installation of the distal end portion of the cannula in the passage, rotating the cannula about the axis thereof to lay the outrigger over against the skin of the recipient, and applying skin attachable hold-down means over the outrigger to detachably secure the cannula to the skin, at least crosswise of its axis, and rotationally thereof.

2. The method according to claim 1 wherein the outrigger projects relatively radially outwardly from the cylindrical outline of the cannula at the outer periphery thereof, to the extent that when the hilt of a relatively inner cannula telescopically engaged in the bore of the first mentioned cannula, is gripped with one hand to advance the first mentioned cannula toward the passage during the installation of the distal end portion of the first mentioned cannula therein, the user can apply one finger of his/her one hand to the outrigger, to drive the first mentioned cannula relatively forward toward the puncture in the skin and disengage the relatively inner cannula from the bore of the first mentioned cannula.

3. The method according to claim 1 further comprising connecting the auxiliary apparatus to the cannula, at the proximal end portion thereof, before the cannula is rotated about the axis thereof to lay the outrigger over against the skin of the recipient.

4. The method according to claim 1 wherein an elongated strip of adhesive tape is applied over the outrigger along a parallel to the axis of the cannula.

5. A catheter which is insertable into a subcutaneous passage in the body of a human or animal recipient which is living or has been recently living, for indwelling therein while blood or other liquid is transmitted through the catheter between the passage and an auxiliary apparatus external to the recipient, comprising:

a pair of elongated relatively inner and outer cannulae which have longitudinal axes and elongated bores extending therethrough along the axes thereof, and the relatively inner of which cannulae is telescopically engageable in and disengageable from the bore of the relatively outer cannula when the respective cannulae are coaxially aligned with one another along the respective longitudinal axes thereof, the relatively outer cannula having relatively proximal and distal ends spaced apart from one another along the longitudinal axis thereof, an outer periphery circumposed about the longitudinal axis thereof between the respective ends thereof, a cylindrical outline at the outer periphery thereof, and a cylindrical surface circumposed about the longitudinal axis thereof on the cylindrical outline thereof, the relatively inner cannula having a shank which is telescopically engageable in and through the bore of the relatively outer cannula from the proximal end thereof, and a hilt which is disposed on the shank and adapted to abut the proximal end of the relatively outer cannula when the shank has extended through the bore of the relatively outer cannula to the extent that the shank projects relatively outwardly beyond the distal end of the relatively outer cannula to form a puncturing tip thereon for the catheter, the proximal end portion of the relatively outer cannula having a pusher tab relatively radially upstanding on the cylindrical surface thereof, which projects relatively radially outwardly from the cylindrical outline of the relatively outer cannula at the outer periphery thereof, to the extent that when a user grips the hilt of the relatively inner cannula with one hand to advance the distal end portion of the relatively outer cannula into a passage of a recipient and disengage the relatively inner cannula from the bore of the relatively outer cannula, he/she can apply one finger of his/her one hand to the tab, to drive the relatively outer cannula relatively forward toward the puncture in the skin of the recipient, but the tab being less than a quadrant in angular extent about the proximal end portion of the relatively outer cannula circumferentially thereof, so that during the advancement of the distal end portion of the relatively outer cannula into the passage of the recipient, the tab can be angularly oriented about the axis of the relatively outer cannula to upstand at a location on the opposite side of the axis of the relatively outer cannula from the skin of the recipient, but afterward, when the distal end portion of the relatively outer cannula is inserted in the passage below the skin, the relatively outer cannula can be rotated about the axis thereof to lay the tab over against the skin of the recipient while skin attachable hold-down means are applied over the tab to detachably secure the relatively outer cannula to the skin, at least crosswise of its axis and rotationally thereof, and the tab taking the form of a stud which is spaced apart from the proximal end of the relatively outer cannula, forwardly of its axis on the cylindrical surface thereof, and is ancipital longitudinally of the relatively outer cannula.

6. The catheter according to claim 5 wherein the stud has a relatively reduced diameter neck which is relatively radially upstanding on the surface of the proximal end portion of the relatively outer cannula, in an axial plane thereof, and has a head at the top thereof, which is supported on the neck and is relatively enlarged to it in the axial plane of the relatively outer cannula.

7. The catheter according to claim 5 wherein the proximal and distal end portions of the relatively outer cannula are relatively enlarged and reduced in diameter, respectively, at the cylindrical surface of the relatively outer cannula, so that the distal end portion of the relatively outer cannula forms a puncture insertable sheath for the shank of the relatively inner cannula, and the proximal end portion of the relatively outer cannula forms a relatively radially enlarged hub at the proximal end of the sheath.

8. The catheter according to claim 5 wherein the cylindrical surface on the proximal end portion of the relatively outer cannula has an annular flange circumposed thereabout at the proximal end of the relatively outer cannula, but the flange projects relatively radially outwardly from the cylindrical surface on the proximal end portion of the relatively outer cannula, to a substantially lesser extent than the tab.

9. An elongated relatively outer cannula for assembly with a relatively inner cannula to form a catheter which is insertable into a subcutaneous passage in the body of a human or animal recipient which is living or has recently been living, for indwelling therein while blood or other liquid is transmitted through the catheter between the passage and an auxiliary apparatus external to the recipient, comprising:

an elongated tubular member which has a longitudinal axis and an elongated bore extending therethrough along the axis thereof, the tubular member having relatively proximal and distal ends spaced apart from one another along the longitudinal axis thereof, an outer periphery circumposed about the longitudinal axis thereof between the respective ends thereof, a cylindrical outline at the outer periphery thereof, and a cylindrical surface circumposed about the longitudinal axis thereof on the cylindrical outline thereof, the proximal and distal end portions of the tubular member being relatively enlarged and reduced in diameter, respectively, at the cylindrical surface of the tubular member, so that the distal end portion of the tubular member forms a puncture insertable sheath for the distal end portion of the relatively inner cannula, and the proximal end portion of the tubular member forms a relatively radially enlarged hub at the proximal end of the sheath, for the proximal end portion of the relatively inner cannula, the proximal end portion of the tubular member having a pusher tab relatively radially upstanding on the cylindrical surface thereof, which projects relatively radially outwardly from the cylindrical outline of the tubular member at the outer periphery thereof, to the extent that when a user grips the relatively inner cannula with one hand to advance the distal end portion of the tubular member into a passage and disengage the relatively inner cannula from the bore of the tubular member, he/she can apply one finger of his/her one hand to the tab, to drive the tubular member relatively forward toward the puncture in the skin of the recipient, but the tab being less than a quadrant in angular extent about the proximal end portion of the tubular member circumferentially thereof, so that during the advancement of the distal end portion of the tubular member into the passage of the recipient, the tab can be angularly oriented about the axis of the tubular member to upstand at a location on the opposite side of the axis of the tubular member from the skin of the recipient, but afterward, when the distal end portion of the tubular member is inserted in the passage below the skin, the tubular member can be rotated about the axis thereof to lay the tab over against the skin of the recipient while skin attachable hold-down means are applied over the tab to detachably secure the tubular member to the skin, at least crosswise of its axis and rotationally thereof, and the tab taking the form of a stud which is spaced apart from the proximal end of the tubular member, forwardly of its axis on the cylindrical surface thereof, and is ancipital longitudinally of the tubular member.

10. The relatively outer cannula according to claim 9 wherein the stud has a relatively reduced diameter neck which is relatively radially upstanding on the surface of the proximal end portion of the tubular member, in an axial plane thereof, and has a head at the top thereof, which is supported on the neck and is relatively enlarged to it in the axial plane of the tubular member.

11. The relatively outer cannula according to claim 9 wherein the cylindrical surface on the proximal end portion of the tubular member has an annular flange circumposed thereabout at the proximal end of the tubular member, but the flange projects relatively radially outwardly from the cylindrical surface on the proximal end portion of the tubular member, to a substantially lesser extent than the tab.

12. A catheter which is insertable into a subcutaneous passage in the body of a human or animal recipient which is living or has been recently living, for indwelling therein while blood or other liquid is transmitted through the catheter between the passage and an auxiliary apparatus external to the recipient, comprising:

a pair of elongated relatively inner and outer cannulae which have longitudinal axes and elongated bores extending therethrough along the axes thereof, and the relatively inner of which cannulae is telescopically engageable in and disengageable from the bore of the relatively outer cannula when the respective cannulae are coaxially aligned with one another along the respective longitudinal axes thereof, the relatively outer cannula having relatively proximal and distal ends spaced apart from one another along the longitudinal axis thereof, an outer periphery circumposed about the longitudinal axis thereof between the respective ends thereof, a generally cylindrical outline at the outer periphery thereof, a generally cylindrical surface circumposed about the longitudinal axis thereof on the cylindrical outline thereof, and a band of ambient atmosphere circumposed about the outer periphery thereof at the cylindrical surface thereof, the band of ambient atmosphere having four successive quadrants circumferentially of the surface, the relatively inner cannula having a shank which is telescopically engageable in and through the bore of the relatively outer cannula from the proximal end thereof, and a hilt which is disposed on the shank and adapted to abut the proximal end of the relatively outer cannula when the shank has extended through the bore of the relatively outer cannula to the extent that the shank projects relatively outwardly beyond the distal end of the relatively outer cannula to form a puncturing tip thereon for the catheter, the proximal end portion of the relatively outer cannula having a pusher tab relatively radially upstanding on the cylindrical surface thereof, which is rigidly connected to the relatively outer cannula in the directions lengthwise the longitudinal axis thereof, and projects relatively radially outwardly from the generally cylindrical outline of the relatively outer cannula at the outer periphery thereof, to the extent that when a user grips the hilt of the relatively inner cannula with one hand to advance the distal end portion of the relatively outer cannula into a passage of a recipient and disengage the relatively inner cannula from the bore of the relatively outer cannula, he/she can apply one finger of his/her one hand to the tab, to drive the relatively outer cannula relatively forward toward the puncture in the skin of the recipient, but the tab being less than one of the four quadrants in angular extent about the proximal end portion of the relatively outer cannula circumferentially thereof, and the remaining three quadrants of ambient atmosphere thereabout being open and unobstructed circumferentially of the surface on the relatively outer cannula, so that during the advancement of the distal end portion of the relatively outer cannula into the passage of the recipient, the tab can be angularly oriented about the axis of the relatively outer cannula to upstand at a location on the opposite side of the axis of the relatively outer cannula from the skin of the recipient, but afterward, when the distal end portion of the relatively outer cannula is inserted in the passage below the skin, the tab can be rotated about the longitudinal axis of the relatively outer cannula, if desired, and laid over against the skin of the recipient while skin-attachable hold down means are applied over the tab to detachably secure the relatively outer cannula to the skin, at least crosswise of its axis and rotationally thereof.

13. The catheter according to claim 12 wherein the tab is also rigidly connected to the relatively outer cannula in directions crosswise and rotational of the longitudinal axis thereof.

14. The catheter according to claim 12 wherein the tab is ancipital longitudinally of the relatively outer cannula.

15. The catheter according to claim 14 wherein the tab takes the form of a stud which is spaced apart from the proximal end of the relatively outer cannula, forwardly of its axis on the cylindrical surface thereof.

16. The catheter according to claim 12 wherein the proximal and distal end portions of the relatively outer cannula are relatively enlarged and reduced in diameter, respectively, at the cylindrical surface of the relatively outer cannula, so that the distal end portion of the relatively outer cannula forms a puncture insertable sheath for the shank of the relatively inner cannula, and the proximal end portion of the relatively outer cannula forms a relatively radially enlarged hub at the proximal end of the sheath.

* * * * *